United States Patent
De Laat

(10) Patent No.: US 11,717,477 B2
(45) Date of Patent: Aug. 8, 2023

(54) VAGINAL SYSTEMIC DRUG DELIVERY

(71) Applicant: LiGalli B.V., The Hague (NL)

(72) Inventor: Wilhelmus Nicolaas Gerardus Maria De Laat, The Hague (NL)

(73) Assignee: LiGalli B.V., The Hague (NL)

(*) Notice: Subject to any disclaimer, the term of this patent is extended or adjusted under 35 U.S.C. 154(b) by 0 days.

(21) Appl. No.: 16/963,764

(22) PCT Filed: Apr. 10, 2019

(86) PCT No.: PCT/EP2019/059126
§ 371 (c)(1),
(2) Date: Jul. 21, 2020

(87) PCT Pub. No.: WO2019/201713
PCT Pub. Date: Oct. 24, 2019

(65) Prior Publication Data
US 2021/0038507 A1 Feb. 11, 2021

(30) Foreign Application Priority Data
Apr. 10, 2018 (EP) .................... 18166624

(51) Int. Cl.
*A61K 9/00* (2006.01)
*A61K 31/216* (2006.01)
(Continued)

(52) U.S. Cl.
CPC ............ *A61K 9/0036* (2013.01); *A61K 31/04* (2013.01); *A61K 31/216* (2013.01);
(Continued)

(58) Field of Classification Search
CPC ............. A61K 31/5513; A61K 31/428; A61K 9/0034; A61K 31/465; A61K 31/485;
(Continued)

(56) References Cited

U.S. PATENT DOCUMENTS

| 5,928,195 A * | 7/1999 | Malamud .......... A61M 5/14593 |
| | | 604/141 |
| 2006/0084848 A1* | 4/2006 | Mitchnick .............. A61B 5/411 |
| | | 600/301 |
| 2012/0202742 A1 | 8/2012 | Ron et al. |

FOREIGN PATENT DOCUMENTS

| CN | 107405299 A | 11/2017 |
| EP | 3153137 A1 | 4/2017 |

(Continued)

OTHER PUBLICATIONS

Woolfson et al., Design of a silicone reservoir intravaginal ring for the delivery of oxybutynin, Journal of Controlled Disease, vol. 91, No. 3, Sep. 4, 2003, p. 465-476.

*Primary Examiner* — Jianfeng Song
(74) *Attorney, Agent, or Firm* — Peter W. Schroen; Bret E. Field; Bozicevic, Field & Francis LLP

(57) ABSTRACT

The present invention relates to a therapeutically active compound for the treatment of a medical condition, wherein the therapeutically active compound is administered in liquid formulation via the vagina by using an intravaginal ring. The present invention further relates to a therapeutically active compound selected from the group consisting of oxybutynin and other anti-muscarinic compounds, gonadotropin-releasing hormone (GnRH) and derivatives, both agonists and antagonists, nitroglycerin and other directly or indirectly acting cGMP enhancers, buprenorphine and other agonistic, antagonistic or partial (ant)agonistic opioids, nicotine and derivatives, lorazepam and other benzodiazepines, insulin and other blood glucose regulating compounds, FSH and other hormones for ovulation stimulation, pramipexol and other dopamine agonists, oxytocin and other hypothalamic peptides for the treatment of a medical condition, wherein the therapeutically active compound is (Continued)

Figure 1:
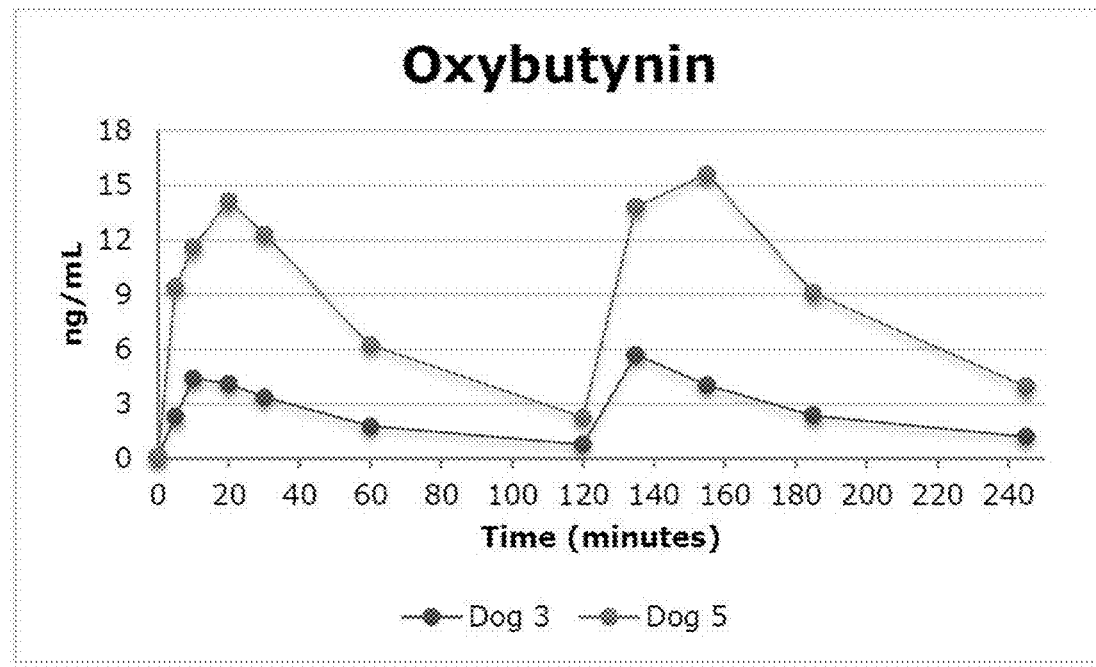

administered in liquid formulation via the vagina by using an intravaginal ring.

19 Claims, 4 Drawing Sheets

(51) Int. Cl.
| | |
|---|---|
| *A61K 38/09* | (2006.01) |
| *A61K 31/428* | (2006.01) |
| *A61K 31/04* | (2006.01) |
| *A61K 31/485* | (2006.01) |
| *A61K 31/465* | (2006.01) |
| *A61K 31/5513* | (2006.01) |
| *A61K 38/28* | (2006.01) |
| *A61K 38/24* | (2006.01) |
| *A61P 15/08* | (2006.01) |
| *A61K 9/08* | (2006.01) |

(52) U.S. Cl.
CPC .......... *A61K 31/428* (2013.01); *A61K 31/465* (2013.01); *A61K 31/485* (2013.01); *A61K 31/5513* (2013.01); *A61K 38/09* (2013.01); *A61K 38/24* (2013.01); *A61K 38/28* (2013.01); *A61P 15/08* (2018.01); *A61K 9/08* (2013.01)

(58) Field of Classification Search
CPC ........ A61K 38/28; A61K 38/09; A61K 47/02; A61K 9/08; A61K 38/24; A61K 31/216; A61K 31/04; A61P 5/24; A61P 9/00; A61P 15/08; A61P 13/10; A61P 35/00; A61P 25/04; A61P 3/10; A61P 25/16
See application file for complete search history.

(56) References Cited

FOREIGN PATENT DOCUMENTS

| | | | | |
|---|---|---|---|---|
| JP | 2016-509883 A | 4/2016 | | |
| WO | WO9956934 A1 | 11/1999 | | |
| WO | WO2011005709 A2 | 1/2011 | | |
| WO | WO2011121604 A2 | 10/2011 | | |
| WO | WO-2014135521 A1 * | 9/2014 | ............ | A61F 6/142 |
| WO | WO2014135521 A1 | 9/2014 | | |

* cited by examiner

VAGINAL SYSTEMIC DRUG DELIVERY

The present invention relates to a therapeutically active compound to be absorbed in the circulatory system for use in the treatment of a medical condition, wherein the therapeutically active compound is administered via the vagina.

At present the vagina is not yet a common route for administering therapeutic compounds other than for gynecological indications, like contraception, labour induction, treatment of vaginal infections, local menopaul atrophia symptoms, or other topical indications for nearby target organs (bladder, uterus, cervix). Such indications are usually limited to the reproductive system and/or do not work systemically. Known intravaginal delivery systems take usually the form of solid or semi-solid therapeutic formulations such as tablets, capsules, liquid preparations, vaginal films and foams. Hormones for contraception are also known to be administered via resinous vaginal rings containing the hormones in a predetermined concentration, such as NuvaRing®. In these rings the active compound is dispersed in the resin and released over time. The disadvantage of such rings is that the release pattern is pre-determined and cannot be adjusted during treatment. Moreover, the dosage of those rings is not completely stable over time, but gradually diminishes. It is not possible to intermittently release the compound and therefore pulsed treatment, or on-demand treatment, cannot be achieved. Moreover, such rings are only suitable for medicaments that can be dissolved or dispersed in the resin and can be released from the resin in the vagina, thus excluding for instance peptides and larger molecules.

Oral drug delivery is the largest part and the most preferred route of conventional drug administration. But oral drug delivery has many known disadvantages, such as nausea, stomach problems, "first-pass" effect, enzymatic degradation, low bioavailability, spiking, short therapeutic window.

Many diseases show circadian rythms in their pathophysiology, such as asthma, angina pectoris, rheuma,ulcers and hypertension. Treatment of such diseases requires pulsatile drug delivery. Many other conditions require pulsatile release of compounds as well, like hormone secretions, such as GnRH, FSH, LH, LHRH, estrogen and progestogens, TSH and insulin.

Next to delivering the drug in the right dose and in the right interval (like pulsatile), it is important to deliver the drug at the right place. It has been proven that there is an extra beneficial "local effect" when delivering the drug close to the target organ.

It is also important to deliver the drug at the right moment, certainly in diseases with circadian rythms, defined as chronopharmacotherapy. Also, in the treatment of symptoms like pain being able to deliver the drug on the right moment is of importance.

It is therefore the object of the present invention to deliver therapeutically active compounds, to be absorbed in the circulatory system, via the vagina.

In the research leading to the invention the potential of programmed vaginal drug administration was explored by investigating the plasma concentration profiles of six water-soluble compounds (and their metabolites) of varying molecular size, lipophilicity and chemical structure (Table 1) in Beagle dogs following vaginal drug administration in liquid formulation.

TABLE 1

| Drug | Molecular weight | Chemical class | Indication |
|---|---|---|---|
| Oxybutinin | 357 | heterocyclic | Overactive bladder/incontinence |
| GnRH | 1212 | decapeptide | gynecology/fertility |
| Nitroglycerin | 227 | simple ester | cardiovascular/angina, heart failure |
| Buprenorphine | 468 | opioid | Chronic pain, opiate addiction |
| Nicotine | 162 | alkaloid | Smoking cessation, cognitive impairment |
| Lorazepam | 321 | benzodiazepine | Sleep impairment, anxiety |

Absorption after intra-vaginal administration was confirmed for all test compounds, including GnRH, a native peptide with a molecular weight of 1212. For nitroglycerin, no detectable concentrations of the parent compound could be observed. However, analysis of two well-known metabolites showed rapid and efficient absorption, implying fast nitroglycerin absorption as well. These results showed that the vagina is an unexpectedly useful alternative dosing route for these compounds, in particular when administered in liquid formulation. The dosage can be much lower than when administration takes place via the conventional routes, such as by enteral or parenteral administration, in particular oral or intramuscular administration.

The invention therefore relates to a therapeutically active compound to be absorbed in the circulatory system for the treatment of a medical condition, wherein the therapeutically active compound is administered in liquid formulation via the vagina by using an intravaginal ring. The ring allows delivery of the drug in the right dose, in the right interval, in the right place and at the right time. Using vaginal drug delivery with a ring which comprises a container for the therapeutic compound, a pump for releasing the compound and electronics for controlling the delivery has many advantages, in particular for scheduled (like pulsed or tapered) delivery, scheduled complex dosing or adjusted dosing, lower dosages leading to less liver toxicity, stable serum levels, the avoidance of the so-called "first-pass effect", high compliance, high convenience, discretion. Administering the drug in liquid form to the vagina by means of an intravaginal ring has many other advantages as well, such as the fact that it can be both inserted and removed by the person carrying the ring herself. The ring has a reservoir for the drug and can thus be used for an extended time period thus avoiding the need for frequent insertion and removal. Drugs administered in liquid formulation in the vagina via a ring are now found to be absorbed in the body, where they exert systemic activity. In addition, the ring is user controlled and patient empowered. This means that the amount of drug released from the ring and the time at which, or the schedule according to which, the release takes place can be adjusted from outside the patient, i.e. remote. This can be done by a medically qualified person but also by the user herself. Drug administration via the vagina leads to fewer side effects and complications.

The ring can also comprise diagnostic means, for example for detecting drug levels in the vaginal mucosa. The release of the therapeutically active compound can be adjusted in response to the diagnostic parameters detected in a ring with combined drud delivery as well as diagnostic capabilities. Finally, a temperature sensor will objectively confirm the patient's compliance to the prescribed medication by logging the body temperature during the time the ring is inserted.

The invention can be used for all therapeutic compounds that can be absorbed in the body through the vaginal mucosa. Such compounds logically include women's health medicines like reproductive (releasing) hormones and antagonists thereof.

The invention relates in particular to administration of gynecological hormones where other schedules (like pulsatility) than the continuous dosage are required, where parenteral dosing is required or where local action provides added value and/or leads to avoidance of extra invasive handling. Such type of administration is clearly superior to the existing methods. Examples are the administration of a Selective Progesterone Receptor Modulator (SPRM), necessitating parenteral administration, or a progesterone containing ring for contraception, where the invasive insertion of a progesterone containing IUD can be avoided, and local action and dose adjusting provide a means for cycle control that does at present not exist. Another example is an oxytocin containing ring where pulsatile administration is required. Furthermore, intravaginal administration is a useful alternative route in cases of low bioavailability after oral intake (e.g. alendronin acid (Fosamax™) for osteoporosis treatment).

More in particular, the invention relates to a therapeutically active compound selected from the group consisting of oxybutynin, gonadotropin-releasing hormone (GnRH), nitroglycerin, buprenorphine, nicotine, lorazepam, insulin, FSH, GnRH-antagonist and pramipexole and oxytocin for a medical condition, wherein the therapeutically active compound is administered in liquid formulation via the vagina by using an intravaginal ring.

In one embodiment, the compound is oxybutynin and the medical condition is Over Active Bladder (OAB) or urge incontinence. The dosage is 5-20 mg/day. All medications lead to frequent dose-dependent side-effects, often necessitating discontinuation of treatment. It has been found that avoiding the administration per os, and thus bypassing the so called "first-pass effect" (via the transdermal route or via a ring) clearly improves the treatment window by allowing a higher dose and/or lowering the side effects. Vaginal delivery of this drug, thus bypassing the first-pass effect, with the possibility of dose adjustment, with the possibility of pulsatile administration, with the existence of local effect and maybe of on-demand administration in case of an approaching involuntary bladder contraction, will clearly add value to the currently insufficient treatment options. The release rates of the ring are 0.1 mg-20 mg/day.

In another embodiment of the invention, the therapeutically active compound is GnRH. This compound is administered for the treatment of infertility. In general, it is used during the treatment of an IVF hyperstimulation cycle, to prevent a premature ovum maturation or ovulation. More specifically, it is also used for treatment of patients with hypogonadotropic, hypo-estrogenic amenorhhoea. The diagnosis is called the Kallmann syndrome if combined with anosmia (the inability to smell).The treatment is only effective if the GnRH is administered parenterally and in a pulsatile manner (pulse every 90 minutes, dose 10-20 µg/pulse). Next to that GnRH is also used for treatment of diseases like endometriosis and fibromas, pubertas praecox, endometrium carcinoma and potentially breast cancer. GnRH antagonists (Ganirelix, Group 2) are prescribed for the same indications.

In a further embodiment the compound is nitroglycerin, used in cases of hart problems, like treatment or prevention of angina pectoris. On-demand function of a ring offers advantages over a patch, and the inherent ambulatory status of ring usage offers advantages over a subcutaneous/subclavian line with a pump, making the patient non-ambulatory. In another embodiment, the compound is buprenorphine and the medical condition is pain.

The compound is usually prescribed in either a patch formulation (release rate 5-70 µg/hr) or as injection (0.3 mg/ml). On-demand function of a ring, with adjustable dosage and timing offers strong advantages.

A further embodiment of the invention relates to nicotine for the indication of assisted smoking cessation or treatment of abstinence symptoms. Nicotine has also been suggested to be implied in the beginning of Alzheimer disease. In the prior art there are patches (7-24 mg/day) or chewing gums (2-4 mg per piece). There is a twofold disadvantage of those formulations. For treating smoking cessation successfully, one would ideally mimick the nicotine release during real smoking in timing and concentration and then subsequently "taper" the height of these concentrations in time and gradually also increase the intervals between them. Neither can be achieved with gums or patches. Administration of nicotine by means of delivery in the vagina via a intravaginal ring offers self-explanatory advantages compared with the limitations of current possibilities.

A further therapeutically active compound is lorazepam, a long-acting benzodiazepine prescribed for chronic/serious sleeping disorders. It is further prescribed in cases of anxiety/panic disorder and at the start of depression and psychosis. Off-label it is prescribed for alcohol abstinence symptoms. The usual dosage is 0.5-7.5 mg/day. Oral intake of this compound for indication of sleep maintenance has limitations compared to a tapered vaginal administration during a part of the night with a ring.

In a further embodiment, the compound is insulin used for insulin-dependent diabetes. The dosage is based on the serum glucose levels. The compound is usually administered subcutaneously, but other efforts have been made for different sites, like inhalation. The advantages are obvious, certainly if adjusted dosing is based on glucose sensor registration present in the same ring.

In another embodiment, the compound is FSH. This female hormone is prescribed in many Assisted Reproduction Treatment (ART) cycles. It is used in hyperstimulation cycles (IVF), but also in order to stimulate the ovaries to grow oocytes for normal ovulation induction. This hormone is usually administered subcutaneously via daily injections. The initial dosages are between 75-225 I.E. per day, and are then adjusted based on serum levels of female hormones and ultrasonographic measurements of the growing oocytes. Clearly, administration via a ring offers advantages over daily injections, in addition to hitherto unknown potential advantages of the local effect.

In a further embodiment the compound is a GnRH antagonist (e.g.Ganirelix). This medicine is used as a competitive antagonist, primarily used in ART to control ovulation. It is usually administered by subcutaneous injection (0.5 mg,/ml)). Ideally, however, these kinds of compounds are administered in a pulsatile manner. This can be achieved when an intravaginal ring is used for delivery of this compound.

In a further embodiment the compound is pramipexole, a dopamine (D2) agonist. This medicine is used for treatment of Parkinson, and specifically restleg legs. The currently used dosage forms vary between 0.125 and 1 mg. An on-demand function in the ring would improve the current therapeutic arsenal of tablets and slow-release tablets. Bromocryptine, another agonist, is used for treatment of hyperprolactinemic tumors and lactation cessation to lower the prolactin concentration in blood. A dose adjusted therapy and probably pulsatile drug delivery via the ring offers advantages over current available options.

In yet another embodiment the therapeutically active compound is oxytocin. This female hormone is indicated to initiate the process of delivery of the baby and also to stimulate lactation. Sometimes it is also prescribed off-label as a mood stimulant. It is presently available for injection only. It would be better if the compound were administered in a pulsatile manner in line with the physiological release of oxytocin which has a half life time of less than 6 minutes. This becomes possible according to the invention. The usual dosage is 0.5-2 m.u. per infusion, further based on indication and progress.

The therapeutically active compound can also be a compound that has an indication in oncology, such as a glucocorticoid for circadian administration, in particular for tumour suppression.

In another embodiment, the therapeutically active compound is an immunotherapeutic compound for treatment of an oncological condition.

The therapeutically active compound is administered in liquid formulation. The liquid formulation is suitably a solution or stable suspension in a fluid medium that is compatible with the vaginal mucosa. It can be an aqueous solution.

According to the invention, the therapeutically active compound is administered to the vagina by means of a vaginal ring. Such vaginal ring is for example the LiGalli iRing™ described in WO2017/060299. This device comprises a first rigid member having a first and second end, a second rigid member having a third and fourth end, a first flexible member coupled between the first and third ends, and a flexible part coupled between the second and fourth ends. In this device, the first rigid member and/or second rigid member comprises a reservoir holding a medicament to be delivered, an opening, and a pump for pumping the therapeutically active compound out of said opening.

Preferably, the ring is configured such that at least one of the first flexible member and the flexible part is at least partially elastic, and wherein the elasticity of the at least one of the first flexible member and the flexible part is such that:

the device can be squeezed to transform a shape of the device from an extended shape to a collapsed shape for allowing the device to be inserted into a vagina of a user;

the device is pre-biased to assume the extended shape when little to no external force is being applied thereto, said extended shape corresponding to a substantially oval or annular ring shape;

the device assumes a shape substantially corresponding to the extended shape when the device is placed and released at or near the fornix posterior vaginae of a user.

In an alternative embodiment, the intravaginal ring can also comprise sensors for measuring parameters that can be used in the diagnosis of a medical condition. The sensor is for example selected from biochemical sensor, temperature sensor, glucose sensor, contraction sensor (electromyogram (EMG) or pressure), cardiovascular sensor.

Furthermore, the intravaginal ring suitably comprises one or more of the following features: a battery, a transmitter configured for wireless transmission of measurement data corresponding to measurements performed by the sensor and/or measurement data or diagnosis information outputted by the diagnostic sensor, a receiver for wirelessly receiving control commands for remote control the pump and/or the sensor, a transceiver unit combining the receiver and transmitter.

The reservoir of this vaginal ring device is small and can contain only a restricted amount of liquid, in the range of 1-3 ml per container in the ring. It was surprisingly found that small amounts of liquid (dosages of 50 µl) still result in a detectable level in blood or plasma, even in a very short time of less than an hour, in particular less than 30 minutes, more in particular within 10 minutes, even more in particular within 2 minutes. It was even found that the levels reached were higher than can be achieved orally or as a gel applied to the skin, even as high as or higher than, after intramuscular injection.

The outer surface of the ring is preferably substantiality smooth. Suitably, at least one of the first flexible member and the flexible part is at least partially made from an elastic material. The flexible part preferably comprises a second flexible member, a third flexible member, a fourth flexible member, a third rigid member having a fifth and sixth end, a fourth rigid member having a seventh and eight end, wherein the second flexible member is coupled in between the second end and the fifth end, wherein the third flexible member is coupled in between the fourth end and the seventh end; and wherein the fourth flexible member is coupled in between the sixth end and the eight end.

In one embodiment, the second, third, or fourth rigid member comprises a source of electrical energy, such as a battery, for providing electrical energy to said pump and/or diagnostic device, said device further comprising a first flexible electrical connection in between said energy source and said pump and/or diagnostic device, said first flexible electrical connection being accommodated in the flexible member(s) arranged in between the pump and/or diagnostic device and the rigid member that holds the electrical energy source.

Suitably, the pump and the energy source are accommodated in different rigid members among the first, second, third, and fourth rigid members; and/or the diagnostic device and the energy source are accommodated in different rigid members among the first, second, third, and fourth rigid members.

The first, second, third, or fourth rigid member can furthermore comprise a controller for controlling said pump and/or diagnostic device.

The ring can further comprise a sensor for measuring biochemical compounds and/or medicines, such as a hormone levels like oestradiol, luteinizing hormone (LH), and progesterone or glucose, and/or other biochemical parameters and/or medication levels; and/or the first, second, third, or fourth rigid member comprising such sensor, said controller being configured for controlling said pump in dependence of a measurement performed by said sensor.

The ring can further comprise a second flexible electrical connection in between said sensor and said controller, and/or a third flexible electrical connection in between said energy source and said controller, and/or a fourth flexible electrical connection in between said controller and said pump and/or diagnostic device, wherein said second, third, and/or fourth flexible electrical connection is at least partly accommodated in the first, second, third, and/or fourth flexible member.

In one embodiment, the first, second, third, and/or fourth rigid member and the first, second, third, and/or fourth flexible member is formed, preferably by injection moulding, using a respective material composition, and wherein the material composition(s) used for the rigid members differs from the material composition(s) used for the flexible members, wherein the couplings between the flexible and rigid members are preferably fixed, preferably formed during the injection moulding of the flexible and/or rigid members; and/or wherein the material composition used for at least one of the rigid members preferably comprises one or more of the materials of the group consisting of: polyolefin, ABS (acrylonitrile butadiene styrene), PA (polyamide), PBT copolyesters (polybutylene terephthalate), polyethylene, polypropylene, polystyrene, polyester, polyester (PLA and other biosorbable plastics), polycarbonate, polyvinyl chloride, polyethersulfone, polysulfone, and polyetheretherketone; and/or wherein the material composition used for at least one of the flexible members preferably comprises one or more of the materials of the group consisting of: LSR (liquid silicone rubber), thermoplastic elastomers (TPE, TPU), thermoset elastomers such as silicone rubber, butadiene rubber, fluoropolymers, poly(p-xylylene) (parylene), and polyacrylate such as poly(methyl methacrylate) (PMMA).

The ring in the extended shape extends around a central axial axis, wherein an outer diameter of the device, determined in a plane perpendicular to said axial axis, lies in a range between 50 and 70 mm, and more preferably between 55 and 65 mm, wherein an inner diameter of the device, determined in a cross section parallel to the axial axis, lies in a range between 4 and 8 mm, wherein the device preferably has a ring shape with a substantially constant outer diameter and/or wherein an internal diameter of the device, determined in a plane perpendicular to said axial axis, is preferably smaller near at least one of the rigid members.

Suitably, at least one of the rigid members in isolation has a bending strength such that when a force of 0.5N is applied at a force application point that is at a distance of 20 mm relative to a fixation point at which the rigid member is held fixed, a bending angle, which corresponds to angle of rotation related to a rotation about the fixation point of a line that extends between the fixation point and the force application point due to the application of said force, does not exceed 10 degrees.

Preferably, at least one of the flexible members in isolation has a bending strength such that when a force of 0.5N is applied at a force application point that is at a distance of 20 mm relative to a fixation point at which the rigid member is held fixed, a bending angle, which corresponds to a rotation angle related to a rotation about the fixation point of a line that extends between the fixation point and the force application point due to the application of said force, exceeds 30 degrees.

In a further embodiment, the therapeutically active compound is administered on demand. Administration modes can vary from continuous to pulsatile to intermittent to chronic.

The administration of a broad variety of drugs in liquid formulation via the vagina thus leads to rapid (IV-range) systemic absorption resulting in therapeutic drug levels.

Administration of therapeutic compounds in liquid formulation via the vagina can suitably be done with a ring as described in WO2017/060299. Examples of embodiments of the invention using such ring are an insulin delivering ring, an insulin delivering ring with glucose sensor, a oxybutynin ring with bladder contraction sensor, a nitroglycerin ring with CV (cardiovascular) sensor or a buprenorphine ring for opiate withdrawal. The ring can be used for administration of a therapeutic compound or combinations of two or more such compounds but also for measuring parameters that are diagnostic for a medical condition. In an advanced embodiment, the diagnostic and administrative functions are combined in one ring.

In the experiments described in the example, 6 groups of 2 female Beagle dogs received a dual vaginal administration at t=0 and t=125 minutes of either Oxybutynin HCl, Gonadotropin-releasing hormone (GnRH), Buprenorphine, Nitroglycerin, Nicotine or Lorazepam. The compounds were simply dissolved in an aqueous solution only. Blood samples were collected at eleven time points: pre-dose, 5, 10, 20, 30, 60, 120, 135, 155, 185 and 245 minutes after the first dose. Concentrations of the test compound (and metabolites) were determined by LC-MS/MS in plasma samples.

It was found that all test compounds were absorbed by the vaginal mucosal wall following their administration. Even more promising was the speed of absorption: the maximal concentrations observed (Cmax) were reached in all cases within 20 minutes after vaginal administration (Tmax ranged from (<5-20 minutes)), highlighting the potential of vaginal drug administration. Nitroglycerin could not be detected in plasma of dogs following vaginal administration because of its well-known very fast metabolism. However, two metabolites of Nitroglycerin (1,2-Glyceryl dinitrate (1,2-GDN) and 1,3-Glyceryl dinitrate (1,3-GDN)) could be detected in plasma with Tmax values of ≤20 minutes following administration of the parent compound, implying that Nitroglycerin itself was absorbed and metabolized very fast, even before drawing the first blood sample after 5 minutes.

In conclusion, all compounds showed (very) fast absorption across the vaginal mucosal wall, highlighting the potential of this dosing route for administration of systemically- or locally- acting drugs with a wide spectrum of physicochemical properties. The LiGalli iRing™ system ensures a fixed and reproducible location in relation to the vaginal mucosal wall and the reproducible delivery of microliter amounts of drug solution and is thus a particularly suitable means for performing the invention.

In the present application the term "liquid formulation" is intended to encompass a state of matter that is fluid, can flow, can be poured and assumes the shape of the container in which it is held. The liquid formulation as defined herein therefore does not comprise a gel, foam or other semi-solid material.

The term "absorption" refers to the movement of a drug from the site of administration to the bloodstream. For the invention absorption is important because the therapeutically active compound must be absorbed before any medicinal effects can take place.

In this application the terms "drug", "medicament", "therapeutically active compound", "medicine" etc. are used interchangeably and all refer to a compound that is used for treating a medical condition in the human or animal body.

The invention will be further illustrated in the Example that follows and that is not intended to limit the invention in any way.

In the Example reference is made to the following figures:

FIG. 1: Pharmacokinetics of oxybutynin after two intravaginal doses.

Figure 2:
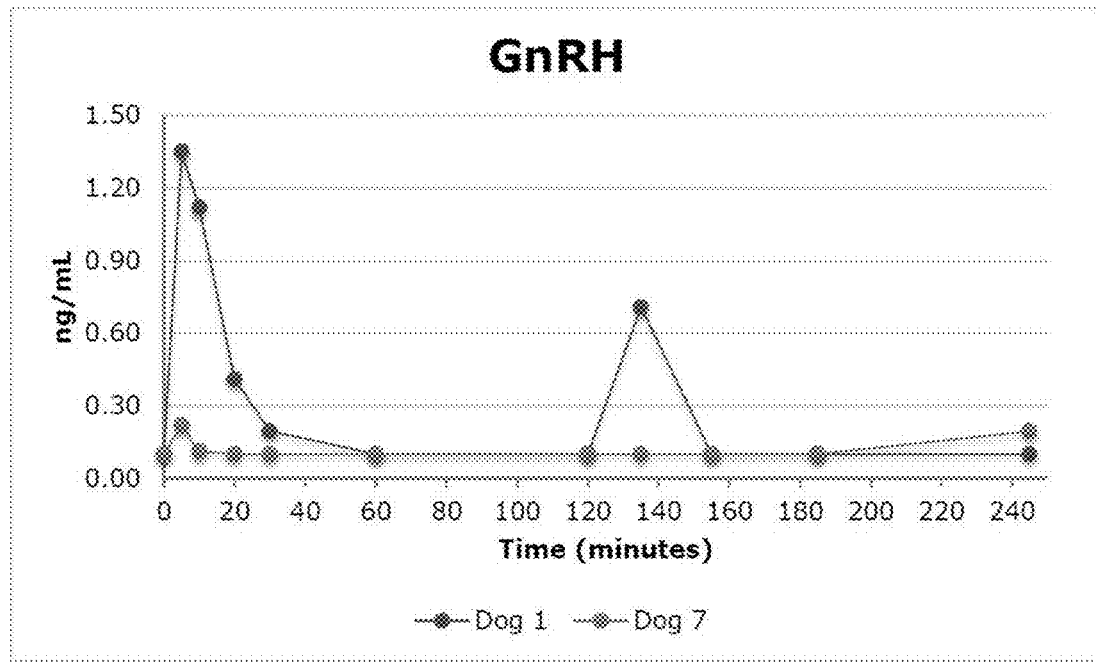

FIG. 2: Pharmacokinetics of GnRH after two intravaginal doses.

Figure 3A:
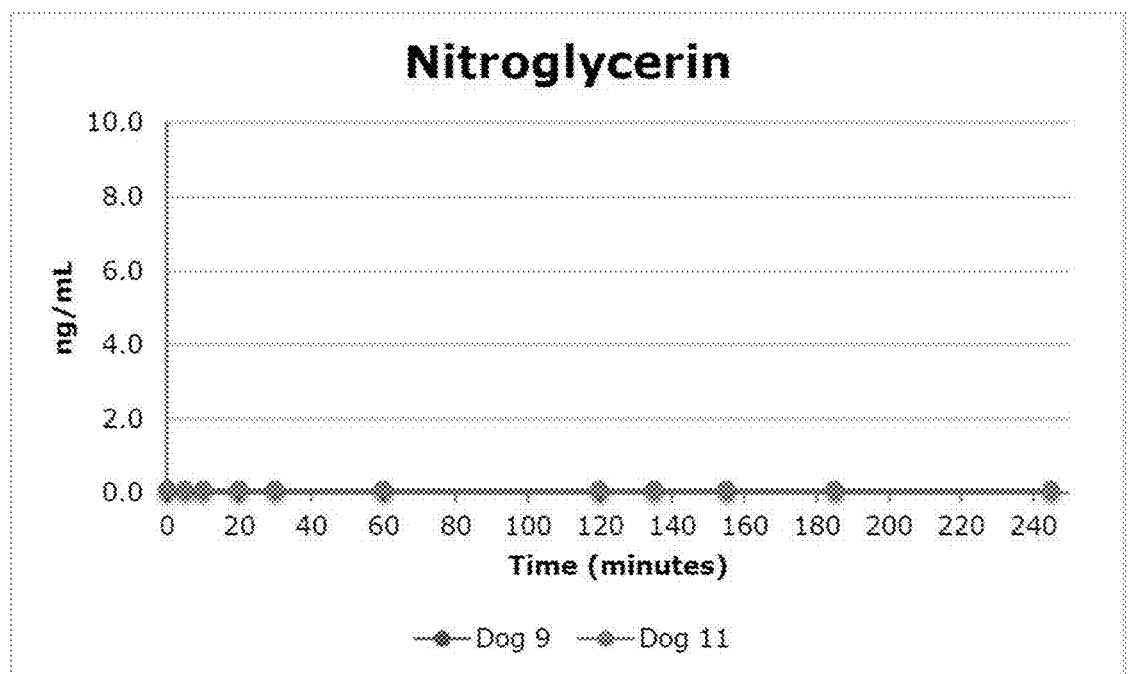

FIG. 3a: Pharmacokinetics of Nitroglycerin after two intravaginal doses.

Figure 3B:
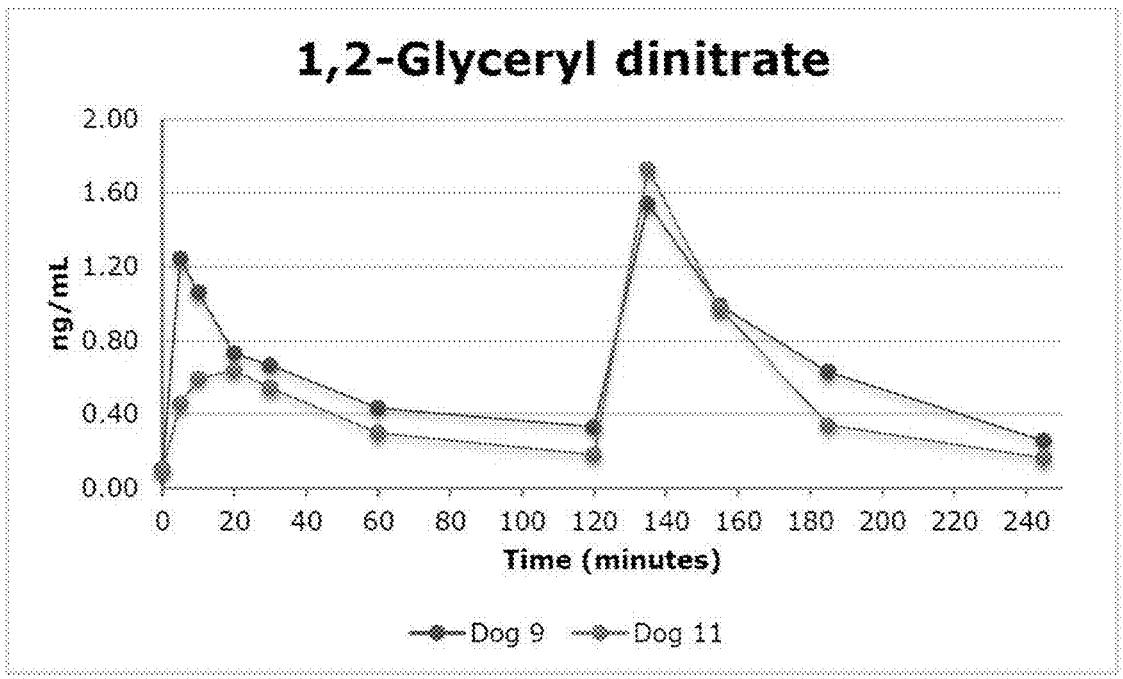

FIG. 3b: Pharmacokinetics of 1,2-Glyceryl dinitrate after two intravaginal doses.

Figure 3C:
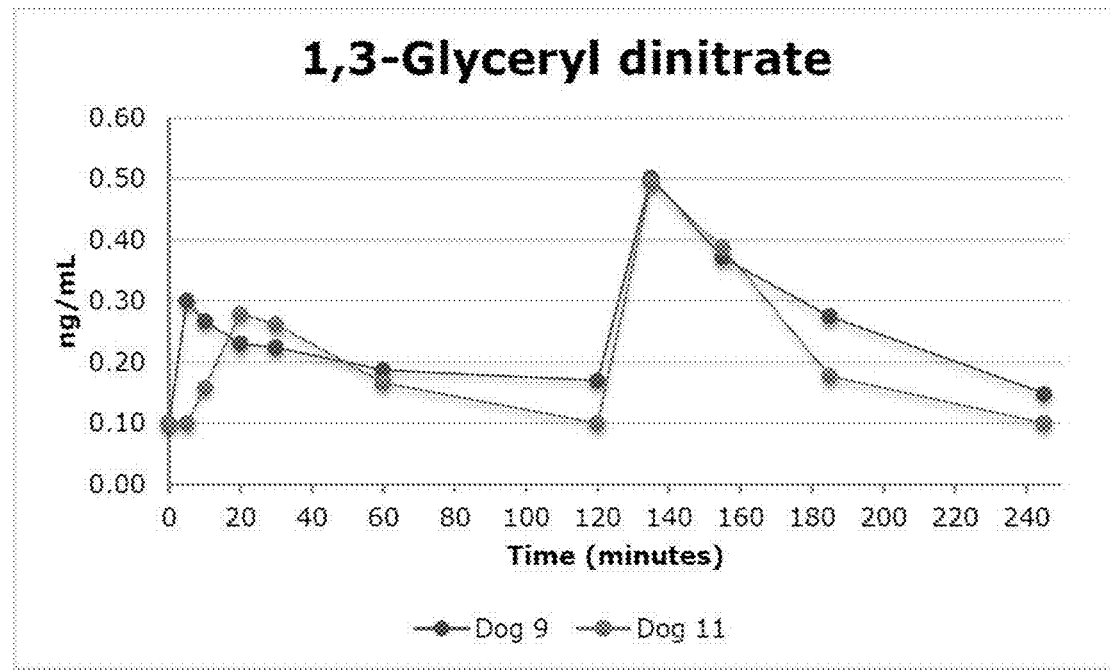

FIG. 3c: Pharmacokinetics of 1,3-Glyceryl dinitrate after two intravaginal doses.

Figure 4:
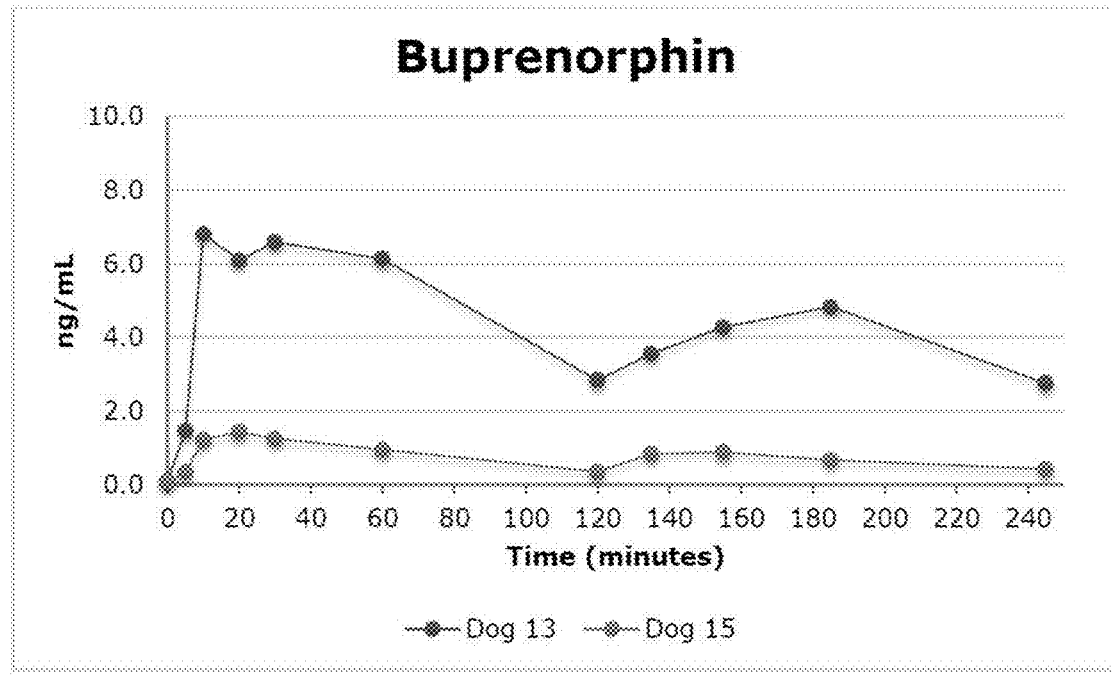

FIG. 4: Pharmacokinetics of Buprenorphine after two intravaginal doses.

Figure 5:
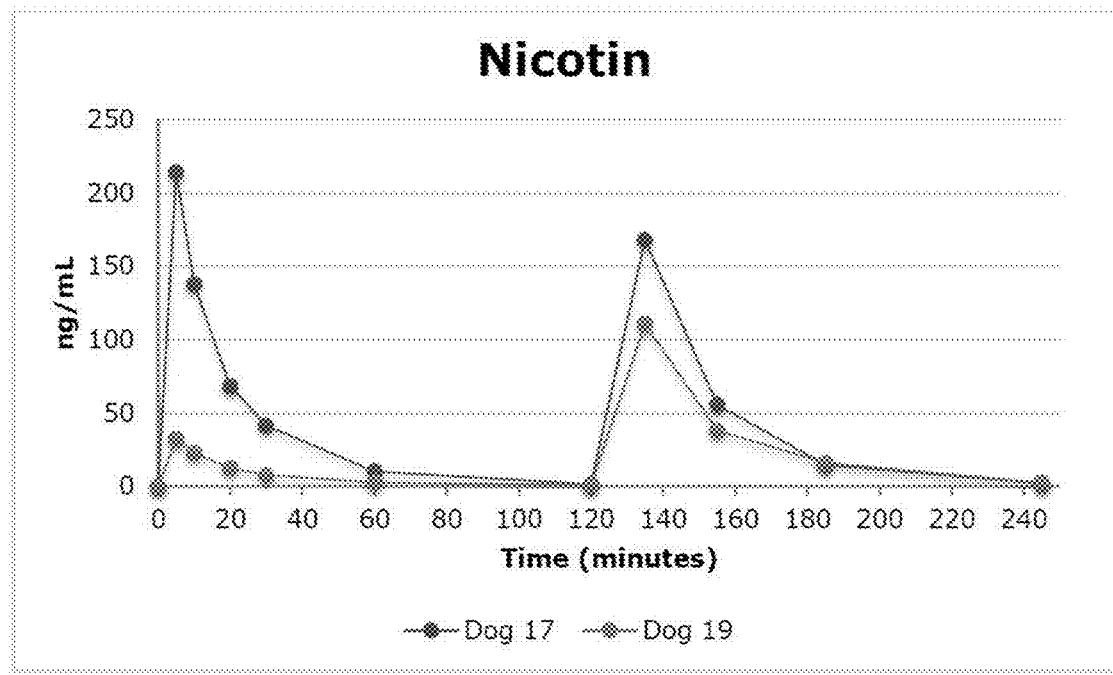

FIG. 5: Pharmacokinetics of Nicotine after two intravaginal doses.

Figure 6:
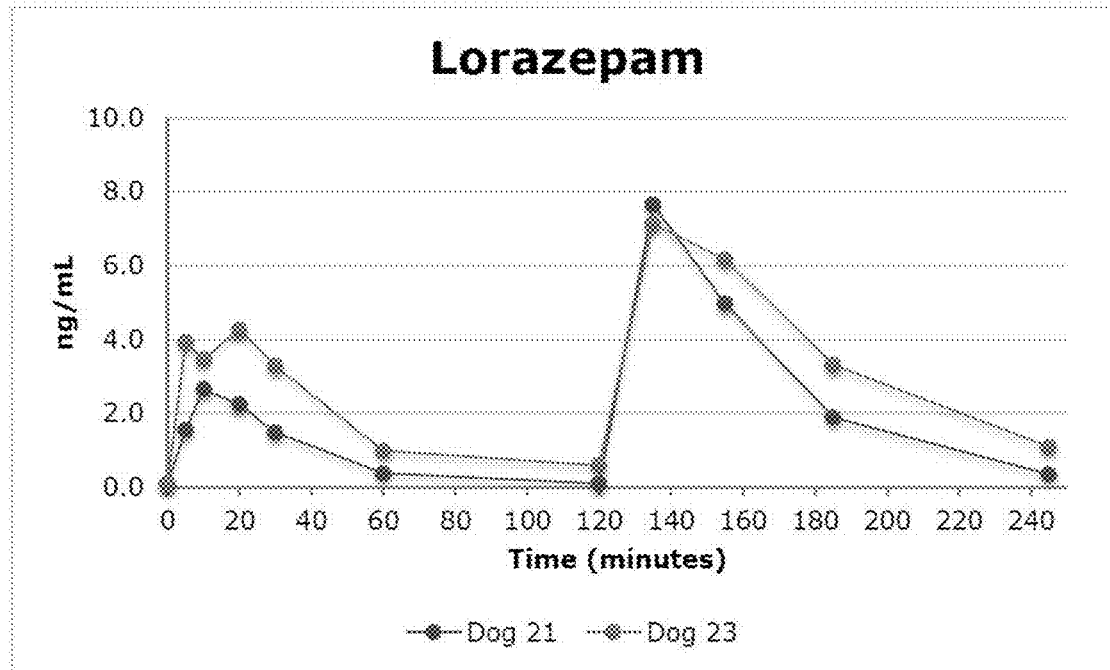

FIG. 6: Pharmacokinetics of Lorazepam after two intravaginal doses.

EXAMPLE

Introduction

The inventors contemplated that the uptake of drugs by the vaginal mucosa could be highly efficient when compared to the oral route. Therefore, this route has the potential of being a first choice application route especially for drugs with low bioavailability, high first-pass effects, or drugs that are ideally administered in a pulsatile manner, exert local effects, or are needed on-demand, or can replace invasive administrations, like subcutaneous, intramuscular or others in chronic diseases. The absence of a first-pass effect may lead to more stable and uniform plasma levels and consequently better efficacy as well as allow lower dosages and thus lead to fewer adverse drug reactions and/or complications.

In order to provide proof of concept, the pharmacokinetic behavior of six different water-soluble test compounds (oxybutynin, Gonadotropin-releasing hormone (GnRH), nitroglycerin, buprenorphine, nicotine and lorazepam) following vaginal application was investigated in Beagle dogs. Beagle dogs are the preferred animal model based on the availability of pharmacokinetic data for other (non-vaginal) dosing routes, allowing for a direct comparison of the vaginal dosing route with more conventional dosing routes.

To study the pharmacokinetics of vaginal dosing of the six compounds to be tested, six groups of two female Beagle dogs received a dual vaginal administration at t=0 and t=125 minutes of either Oxybutynin HCl, GnRH, Buprenorphine, Nitroglycerin, Nicotine or Lorazepam. Blood samples were collected at pre-dose, 5, 10, 20, 30, 60, 120, 135, 155, 185 and 245 minutes after the first dose. Plasma samples were sent to the bioanalysis department of ABL, Assen, for determination of test compound levels by LC-MS/MS. Additional samples obtained from animals receiving Nitroglycerin were also analysed by the same laboratory in order to identify the concentrations of two major metabolites (1,2-Glyceryl dinitrate (1,2-GDN) and 1,3-Glyceryl dinitrate (1,3-GDN) of Nitroglycerin.

Materials and Methods

Twelve female Beagle dogs (Harlan Winkle, Germany) that were ca. 4 months of age and had a body weight of ca. 4-8 kg at dosing time were used in this study. Thirteen days prior to the experimental start date the animals were acclimatized to the laboratory conditions. Upon arrival, the dogs were housed in a quarantine room and checked for overt signs of ill health and anomalies. Animals were kept in rooms ventilated with 9-11 air changes per hour and were maintained at a temperature of 15-21° C. and a relative humidity of 45-75% other than during room cleaning. Lighting was artificial with a sequence of 12 hours light and 12 hours dark. All animals were housed in subgroups of 6 dogs in suitable dog cages. Each dog was uniquely identified with a number that was programmed in a transponder, which was subcutaneously implanted at allocation. Each cage was provided with a card showing the animal identification numbers, the group code and the study code. Dogs were assigned to their groups based on bodyweight.

The dogs received one portion of a commercial dog diet twice daily (in the morning and afternoon). Drinking water was offered ad libitum at all times.

Experimental Design

The study comprised the groups described in the Table 2 below.

TABLE 2

| Group 1 | Test Article | Nominal dose level (mg/animal) | No. dogs |
|---|---|---|---|
| 1 | Oxybutynin HCl | 2 × 2.5 mg 2 | 2 |
| 2 | Gonadotropin-releasing hormone (GnRH) | 2 × 0.5 mg | 2 |
| 3 | Nitroglycerin | 2 × 0.3 mg | 2 |
| 4 | Buprenorphine | 2 × 0.3 mg | 2 |
| 5 | Nicotine | 2 × 5.0 mg | 2 |
| 6 | Lorazepam | 2 × 0.8 mg | 2 |

Conscious dogs were dosed vaginally with 50 μL of the formulated test substance at t=0 and t=125 minutes.

Test Substance Formulation

The formulations were prepared as follows.
Group 1: 50 mg/mL Oxybutynin HCl, prepared in-house
   A solution of 50 mg/mL was prepared in demineralized water. To this end, 50.7 mg of Oxybutynin HCl was weighed in an Eppendorf tube and was subsequently dissolved by adding 1014 mg demineralized water.
Group 2: 10 mg/mL GnRH, prepared in house
   GnRH and its solvent were obtained from a local pharmacy. A solution of 10 mg/mL was prepared in 0.9% NaCl. To this end, to a vial containing 3.2 mg of GnRH 323 mg of a supplied 0.9% NaCl solution was added, which was then transferred into an Eppendorf tube. analysis.
Group 3: 6.4 mg/mL Nitroglycerin, ready to use
   This solution was obtained from a local pharmacy. 1.0 mL of the ready-to-use solution was transferred to an Eppendorf tube by 19 spray releases from the supplied solution.
Group 4: 6 mg/mL Buprenorphine, prepared in-house
   A solution of 6 mg/mL was prepared in demineralized water. This solution was prepared by weighing 6.0 mg of Buprenorphine in an Eppendorf tube and adding 999.2 mg demineralized water.
Group 5: 100 mg/mL Nicotine, ready to use.
   A solution containing 100 mg/mL in propylene glycol was obtained from a Webshop. 1005 mg of this solution was transferred into an Eppendorf tube.
Group 6: 16 mg/mL Lorazepam, prepared in-house
   A solution of 16 mg/mL was prepared in propylene glycol. To this end, 16.9 mg Lorazepam was weighed in an Eppendorf tube and 1086 mg of propylene glycol was added.

Sample Collection and Dose Formulations

Blood samples of ca. 2 mL were collected at pre-dose and ca. 5, 10, 20, 30, 60, 120, 135, 155, 185 and 245 minutes after the first dose in K2-EDTA vials. Plasma samples were prepared, each sample was divided in two aliquots (one sample was shipped for analysis and one sample was kept as a back-up sample). These samples were stored at below −18° C.

Dose solutions were prepared (groups 1, 2, 4 and 6) within 2 hours before dosing. The solutions were kept on ice, protected from light until dosing. Shortly before dosing, the dose solutions were allowed to adjust to room temperature.

The animals received a vaginal dose of 50 μL via a positive-displacement pipette (which is a technically adequate method for dosing during a pilot experiment) at t=0 and t=125 minutes.

Blood samples of ca. 2 mL were collected in K2EDTA vials from the vena jugularis at pre-dose and ca. 5, 10, 20, 30, 60, 120, 135, 155, 185 and 245 minutes after the first dose. Blood samples were kept on ice until further processing to avoid breakdown of the test substances.

Blood was centrifuged at 4° C. for 10 min. at 2000× g between 20 min and 45 min after collection in order to prepare plasma samples. After centrifugation, the plasma was aliquoted into two cryovials and subsequently stored at below −18° C. until shipment to ABL.

Each animal was observed twice daily (morning and afternoon) by cage-side observations. Body weights were determined during acclimatization and one day prior to dosing.

Plasma samples were sent on dry ice to the bioanalytical department of ABL, Assen for determination of drug levels by LC-MS/MS. The analysis was applied to 22 plasma samples per test substance. Calibration samples, quality control samples and blank plasma samples were included. The analytical range was aimed at 0.1-100 ng/mL.

The time schedule for dose administration and collection of blood samples as well as the actual time of dosing and blood sampling is given in Table 3 below. Blood samples were obtained using the Vacutainer system: ca. 2 mL of whole blood was collected in $K_2$-EDTA vials before further processing.

Below are the summaries of the methods that were applied for all 6 compounds that were tested.

Oxybutynin HCl

| | |
|---|---|
| Analytical Range | 0.100-100 ng/mL |
| LC system | Shimadzu Nexera UPLC |
| MS/MS system | Sciex API5500 |
| Sample volume | 50 μL |

Method Description

Oxybutynin was extracted from dog $K_2$-EDTA plasma by a liquid-liquid extraction with TBME. After liquid-liquid extraction the extract was evaporated under a stream of nitrogen and reconstituted in injection solvent. After preparation all samples were injected into the chromatographic system. Chromatographic separation was performed on a Acquity BEH C8 column using gradient elution. An API 5500 tandem mass spectrometer equipped with a Turbo Ion Spray probe operating in the positive multiple reaction monitoring mode was used for quantification.

GnRH

| | |
|---|---|
| Analytical Range | 0.100-100 ng/mL |
| LC system | Shimadzu Nexera UPLC |
| MS/MS system | Sciex API5500 |
| Sample volume | 50 μL |

TABLE 3

| | | Dosing | | Blood sampling | | | | | | | | | | | |
|---|---|---|---|---|---|---|---|---|---|---|---|---|---|---|---|
| Dose | Animal | 0 min | | 5 min | | 10 min | | 20 min | | 30 min | | 60 min | | 120 min | |
| Group | number | Dose 1 | Actual | BL2 | Actual | BL3 | Actual | BL4 | Actual | BL5 | Actual | BL6 | Actual | BL7 | Actual |
| 1 | 5 | 0:00 | 0:00 | 0:05 | 0:07 | 0:10 | 0:10 | 0:20 | 0:22 | 0:30 | 0:37 | 1:00 | 0:59 | 2:00 | 2:01 |
| 1 | 3 | 0:10 | 0:10 | 0:15 | 0:15 | 0:20 | 0:21 | 0:30 | 0:30 | 0:40 | 0:40 | 1:10 | 1:11 | 2:10 | 2:13 |
| 2 | 1 | 0:20 | 0:20 | 0:25 | 0:25 | 0:30 | 0:30 | 0:40 | 0:40 | 0:50 | 0:50 | 1:20 | 1:20 | 2:20 | 2:20 |
| 2 | 7 | 0:30 | 0:30 | 0:35 | 0:40 | 0:40 | 0:42 | 0:50 | 0:50 | 1:00 | 1:00 | 1:30 | 1:35 | 2:30 | 2:35 |
| 3 | 9 | 0:40 | 0:40 | 0:45 | 0:45 | 0:50 | 0:50 | 1:00 | 1:01 | 1:10 | 1:10 | 1:40 | 1:40 | 2:40 | 2:41 |
| 3 | 11 | 0:50 | 0:50 | 0:55 | 0:55 | 1:00 | 1:00 | 1:10 | 1:11 | 1:20 | 1:20 | 1:50 | 1:50 | 2:50 | 2:51 |

| | | Dosing | | Blood sampling | | | | | | | | | |
|---|---|---|---|---|---|---|---|---|---|---|---|---|---|
| Dose | Animal | 125 min | | 135 min | | 155 min | | 185 min | | 245 min | | | |
| Group | number | Dose 2 | Actual | BL8 | Actual | BL9 | Actual | BL10 | Actual | BL11 | Actual | | |
| 1 | 5 | 2:05 | 2:05 | 2:15 | 2:13 | 2:35 | 2:39 | 3:05 | 3:04 | 4:05 | 3:59 | | |
| 1 | 3 | 2:15 | 2:15 | 2:25 | 2:25 | 2:45 | 2:45 | 3:15 | 3:15 | 4:15 | 4:23 | | |
| 2 | 1 | 2:25 | 2:25 | 2:35 | 2:35 | 2:55 | 2:57 | 3:25 | 3:25 | 4:25 | 4:25 | | |
| 2 | 7 | 2:35 | 2:36 | 2:45 | 2:51 | 3:05 | 3:09 | 3:35 | 3:39 | 4:35 | 4:35 | | |
| 3 | 9 | 2:45 | 2:45 | 2:55 | 2:57 | 3:15 | 3:15 | 3:45 | 3:45 | 4:45 | 4:45 | | |
| 3 | 11 | 2:55 | 2:55 | 3:05 | 3:05 | 3:25 | 3:25 | 3:55 | 3:56 | 4:55 | 4:55 | | |

| | | Dosing | | Blood sampling | | | | | | | | | | | |
|---|---|---|---|---|---|---|---|---|---|---|---|---|---|---|---|
| Dose | Animal | 0 min | | 5 min | | 10 min | | 20 min | | 30 min | | 60 min | | 120 min | |
| Group | number | Dose 1 | Actual | BL21 | Actual | BL3 | Actual | BL4 | Actual | BL5 | Actual | BL6 | Actual | BL7 | Actual |
| 4 | 13 | 0:00 | 0:00 | 0:05 | 0:05 | 0:10 | 0:10 | 0:20 | 0:20 | 0:30 | 0:30 | 1:00 | 1:00 | 2:00 | 2:00 |
| 4 | 15 | 0:10 | 0:10 | 0:15 | 0:15 | 0:20 | 0:20 | 0:30 | 0:31 | 0:40 | 0:40 | 1:10 | 1:10 | 2:10 | 2:13 |

TABLE 3-continued

| Dose Group | Animal number | 15 min Dose 2 | Actual | 25 min BL1 | Actual | 35 min BL2 | Actual | 45 min BL3 | Actual | 55 min BL4 | Actual | 85 min BL5 | Actual | 145 min BL6 | Actual |
|---|---|---|---|---|---|---|---|---|---|---|---|---|---|---|---|
| 5 | 17 | 0:20 | 0:20 | 0:25 | 0:25 | 0:30 | 0:30 | 0:40 | 0:40 | 0:50 | 0:50 | 1:20 | 1:20 | 2:20 | 2:20 |
| 5 | 19 | 0:30 | 0:30 | 0:35 | 0:36 | 0:40 | 0:40 | 0:50 | 0:52 | 1:00 | 1:00 | 1:30 | 1:30 | 2:30 | 2:30 |
| 6 | 21 | 0:40 | 0:40 | 0:45 | 0:45 | 0:50 | 0:50 | 1:00 | 1:01 | 1:10 | 1:10 | 1:40 | 1:42 | 2:40 | 2:41 |
| 6 | 23 | 0:50 | 0:50 | 0:55 | 0:55 | 1:00 | 1:00 | 1:10 | 1:10 | 1:20 | 1:20 | 1:50 | 1:50 | 2:50 | 2:50 |

| Dose Group | Animal number | Dosing 125 min Dose 2 | Actual | Blood sampling 135 min BL8 | Actual | 155 min BL9 | Actual | 185 min BL10 | Actual | 245 min BL11 | Actual |
|---|---|---|---|---|---|---|---|---|---|---|---|
| 4 | 13 | 2:05 | 2:05 | 2:15 | 2:15 | 2:35 | 2:35 | 3:05 | 3:07 | 4:05 | 4:05 |
| 4 | 15 | 2:15 | 2:15 | 2:25 | 2:25 | 2:45 | 2:45 | 3:15 | 3:17 | 4:15 | 4:15 |
| 5 | 17 | 2:25 | 2:25 | 2:35 | 2:35 | 2:55 | 2:57 | 3:25 | 3:25 | 4:25 | 4:25 |
| 5 | 19 | 2:35 | 2:35 | 2:45 | 2:46 | 3:05 | 3:05 | 3:35 | 3:35 | 4:35 | 4:35 |
| 6 | 21 | 2:45 | 2:45 | 2:55 | 2:58 | 3:15 | 3:16 | 3:45 | 3:46 | 4:45 | 4:48 |
| 6 | 23 | 2:55 | 2:55 | 3:05 | 3:05 | 3:25 | 3:25 | 3:55 | 3:55 | 4:55 | 4:55 |

Method Description

GnRH was extracted from dog $K_2$-EDTA plasma by a solid phase extraction with Oasis HLB columns. After solid phase extraction the extract was evaporated under a stream of nitrogen and reconstituted in injection solvent. After preparation, all samples were injected into the chromatographic system. Chromatographic separation was performed on an Acquity BEH C8 3.0×100 mm, 1.7 μm column using gradient elution. An API 5500 tandem mass spectrometer equipped with a Turbo Ion Spray probe operating in the positive multiple reaction monitoring mode was used for quantification.

Nitroglycerin

| | |
|---|---|
| Analytical Range | 0.100-100 ng/mL |
| LC system | Shimadzu Nexera UPLC |
| MS/MS system | Sciex API4000 |
| Sample volume | 100 μL |

Method Description

Nitroglycerin was extracted from dog $K_2$-EDTA plasma by a liquid-liquid extraction (LLE) with a mixture of dichloromethane and Methyl tert-Butyl ether. After LLE the extract was evaporated under a stream of nitrogen and reconstituted in injection solvent. After preparation, all samples were injected into the chromatographic system. Chromatographic separation was performed on a Thermo hypersil gold C18 column using gradient elution. An API4000 tandem mass spectrometer equipped with a Turbo Ion Spray probe operating in the negative multiple reaction monitoring mode was used for quantification.

Buprenorphine

| | |
|---|---|
| Analytical Range | 0.100-100 ng/mL |
| LC system | Shimadzu Nexera UPLC |
| MS/MS system | Sciex API4000 |
| Sample volume | 50 μL |

Method Description

Buprenorphine was extracted from dog $K_2$-EDTA plasma by a liquid-liquid extraction (LLE) with Methyl tert-Butyl ether. After the LLE the extract was evaporated under a stream of nitrogen and reconstituted in injection solvent. After preparation, all samples were injected into the chromatographic system. Chromatographic separation was performed on a Thermo Hypersil Gold column using gradient elution. An API4000 tandem mass spectrometer equipped with a Turbo Ion Spray probe operating in the positive multiple reaction monitoring mode was used for quantification.

Nicotine

| | |
|---|---|
| Analytical Range | 0.100-100 ng/mL |
| LC system | Shimadzu Nexera UPLC |
| MS/MS system | Sciex API4000 |
| Sample volume | 50 μL |

Method Description

Nicotine and internal standard Nicotine-D3 were extracted from dog $K_2$-EDTA plasma by precipitation with methanol. After precipitation, the samples were diluted with water and injected into the chromatographic system. Chromatographic separation was performed on a Waters XBridge™ C18 column using gradient elution. An API 4000 tandem mass spectrometer equipped with a TIS probe operated in the multiple reaction monitoring (MRM) in positive mode was used for quantification.

Lorazepam

| | |
|---|---|
| Analytical Range | 0.100-100 ng/mL |
| LC system | Shimadzu Acquity UPLC |
| MS/MS system | Sciex API4000 |
| Sample volume | 50 μL |

Method Description

Lorazepam was extracted from dog $K_2$-EDTA plasma by a liquid-liquid extraction with Methyl tert-Butyl Ether. After liquid-liquid extraction, the extract was evaporated under a stream of nitrogen and reconstituted in injection solvent. After preparation, all samples were injected into the chromatographic system. Chromatographic separation was performed on an Acquity UPLC BEH C8 column using gradient elution. An API4000 tandem mass spectrometer equipped with a Turbo Ion Spray probe operating in the positive multiple reaction monitoring mode was used for quantification.

RESULTS

The measured study sample results for all six test compounds are presented in Table 4.

Oxybutynin HCl

Oxybutynin HCl (FIG. 1) was absorbed quickly following vaginal administration ($T_{max}$ either 10 or 20 min). Oxybutynin HCl was almost completely eliminated from the body at t=120 min. The second dose of Oxybutynin HCl resulted in similar concentrations for both animals. The maximal concentration observed ($C_{max}$) value for one of the animals was more than 3-times higher than for the other, indicating variation in the vaginal absorption of Oxybutynin HCl in Beagle dogs. This might be due to variation in the exact site of dose application, although this procedure was standardized as much as possible. The fact that the relative shape of the concentration vs. time profiles for both dogs was similar after the first as well as the second administration suggests that individual differences in vaginal geometry and mucosal properties may play an important role. It is evident from Table 5 (see below) that acute vaginal administration of an aqueous solution of Oxybutynin HCl in the dog resulted in rapid absorption of the drug as well as plasma levels comparable to those seen in another study on dogs employing either a silastic intra-vaginal ring as well as those observed after either oral or dermal administration in humans (WO2011/163358). Peak levels in the present study were observed substantially faster than those following oral or transdermal administration (Kennelly M J, Rev. Urol., 2010; 12(1): 12-19).

TABLE 5

Comparison of Oxybutynin HCl after two intravaginal doses with other dosing routes

| Species | Dose | Route | $C_{max}$ (ng/mL) | $T_{max}$ (min) | Reference |
|---|---|---|---|---|---|
| Dog | 2.5 (1st) | Vaginal | 4.4 | 10 | Present study |
| Dog | 2.5 (2nd) | Vaginal | 5.7 | 10 | Present study |
| Dog | 2.5 (1st) | Vaginal | 14.1 | 15 | Present study |
| Dog | 2.5 (2nd) | Vaginal | 15.6 | 20 | Present study |
| Dog | 2.5 mg/24 h | Vaginal (ring) | 14.0 | 90 | WO2011163358 |
| Dog | 6.0 mg/24 h | Vaginal (ring) | 18.8 | 90 | WO2011163358 |
| Dog | 10 mg/24 h | Oral | 17.9 | 180 | WO2011163358 |
| Human | 5.0 | Oral | 10.0 | 50 | Kennelly[1] |
| Human | 5.0 | Oral (ext. rel.) | 2.1 | 60 | Kennelly[1] |
| Human | 5.0 | Dermal (patch) | 4.2 | 1500 | Kennelly[1] |
| Human | 100 | Dermal (gel) | 3.2 | 1500 | Kennelly[1] |

[1]Kennelly MJ, Rev. Urol., 2010; 12 (1): 12-19

Gonadotropin-Releasing Hormone (GnRH)

Gonadotropin-releasing hormone (GnRH) (FIG. 2) showed a very high turn-over in both animals. GnRH was rapidly absorbed in both animals after the first dose ($T_{max}$=<5 minutes post-dosing). The elimination of GnRH was very fast as well, with plasma levels falling below the lower-limit-of-quantification (LLOQ) within 60 minutes for both animals. GnRH plasma levels following the second dose administration were lower than those observed after the first dose.

Intra-vaginal GnRH administration in the present study was fast and resulted in plasma levels comparable to those seen in humans after intranasal dosing, as can be observed in Table 6. It is not known which plasma concentrations of GnRH are required for efficacy in e.g. Kallmann syndrome.

TABLE 4

| | Group 1 Oxybutynin HCl | | Group 2 GnRH | | Group 3 Nitroglycerin | | Group 4 Buprenorphine | | Group 5 Nicotine | | Group 6 Lorazepam | |
|---|---|---|---|---|---|---|---|---|---|---|---|---|
| | DOG 3 | DOG 5 | DOG 1 | DOG 7 | DOG 9 | DOG 11 | DOG 13 | DOG 15 | DOG 17 | DOG 19 | DOG 21 | DOG 23 |
| Dose solution (mg/mL) | | | 7.68 | | 7.71 | | 4.73 | | 122 | | 16.6 | |
| Theoretical dose administered (mg) | 2.01 | | 0.38 | | 0.39 | | 0.24 | | 6.10 | | 0.83 | |
| | Plasma concentration (ng/mL) | | Plasma concentration (ng/mL) | | Plasma concentration (ng/mL) | | Plasma concentration (ng/mL) | | Plasma concentration (ng/mL) | | Plasma concentration (ng/mL) | |
| Pre-dose | <LLOQ | <LLOQ | <LLOQ | <LLOQ | <LLOQ | <LLOQ | <LLOQ | <LLOQ | <LLOQ | <LLOQ | <LLOQ | <LLOQ |
| 5 min | 2.28 | 9.42 | 1.35 | 0.22 | <LLOQ | <LLOQ | 1.46 | 0.34 | 214 | 32.3 | 1.55 | 3.93 |
| 10 min | 4.40 | 11.6 | 1.12 | 0.11 | <LLOQ | <LLOQ | 6.82 | 1.22 | 138 | 23.0 | 2.65 | 3.47 |
| 20 min | 4.08 | 14.1 | 0.41 | <LLOQ | <LLOQ | <LLOQ | 6.10 | 1.43 | 68.1 | 12.4 | 2.23 | 4.25 |
| 30 min | 3.36 | 12.3 | 0.20 | <LLOQ | <LLOQ | <LLOQ | 6.59 | 1.25 | 41.6 | 7.87 | 1.49 | 3.28 |
| 60 min | 1.76 | 6.21 | <LLOQ | <LLOQ | <LLOQ | <LLOQ | 6.14 | 0.95 | 10.1 | 2.78 | 0.38 | 0.99 |
| 120 min | 0.76 | 2.24 | <LLOQ | <LLOQ | <LLOQ | <LLOQ | 2.83 | 0.35 | 1.67 | 0.77 | <LLOQ | 0.59 |
| 135 min | 5.69 | 13.8 | 0.71 | <LLOQ | <LLOQ | <LLOQ | 3.56 | 0.83 | 168 | 111 | 7.65 | 7.13 |
| 155 min | 4.00 | 15.6 | <LLOQ | <LLOQ | <LLOQ | <LLOQ | 4.28 | 0.88 | 55.6 | 38.1 | 4.96 | 6.16 |
| 185 min | 2.33 | 9.06 | <LLOQ | <LLOQ | <LLOQ | <LLOQ | 4.84 | 0.67 | 14.7 | 16.2 | 1.89 | 3.32 |
| 245 min | 1.17 | 3.92 | <LLOQ | 0.19 | <LLOQ | <LLOQ | 2.75 | 0.43 | 2.04 | 2.51 | 0.35 | 1.10 |

However, it is anticipated that plasma levels obtained by intra-vaginal dosing might be sufficient in view of the fact that endogenous plasma levels are two orders of magnitude lower (see Table 6).

TABLE 6

Comparison of GnRH after two intravaginal doses with other dosing routes

| Species | Dose (mg) | Route | $C_{max}$ (ng/mL) | $T_{max}$ (min) | Reference |
|---|---|---|---|---|---|
| Dog | 0.5 (1st) | Vaginal | 1.4 | 5 | Present study |
| Dog | 0.5 (2nd) | Vaginal | 0.7 | 10 | Present study |
| Dog | 0.5 (1st) | Vaginal | 0.2 | 5 | Present study |
| Dog | 0.5 (2nd) | Vaginal | 0.2 | 10 | Present study |
| Human | 0.8 | Intranasal | 0.35 | Unknown | Handelsman[1] |
| Human | Endogenous | Endogenous | 0.002 | Not | Araki[2] |

[1]Handelsman DJ, et al., Endocr Rev, 1986; 7 (1), 95-105
[2]Araki S, et al., Endocrinol. Japan, 1986; 33 (4), 457-468

Nitroglycerin

No parent compound concentrations could be detected in plasma from the animals receiving Nitroglycerin (FIG. 3a), which is likely caused by the very short half-life reported for this drug (Lee F W, et al., J Pharmacol Exp Ther, 1990; 255(3): 1222-1229). However, analysis of two well-known metabolites of Nitroglycerin (1,2- and 1,3-Glyceryl dinitrate) showed rapid formation of both metabolites, with peak concentrations at 5 or 20 minutes after dosing the parent compound. The second dose of Nitroglycerin resulted in (slightly) increased plasma concentrations for both metabolites.

Compared to studies using a significantly higher oral dose of Nitroglycerin, the $T_{max}$ values observed for both metabolites in the present study were considerably shorter, although not as fast as those observed following intravenous dosing (Tables 7 and 8). Whereas the maximal concentrations obtained in the present study were not as high as those using the oral formulation, one should note that the dose used in the oral study was considerably higher.

TABLE 7

Comparison of 1,2-GDN after two intravaginal doses with other dosing routes

| Species | Dose (mg) Nitroglycerin | Route | $C_{max}$ (ng/mL) 1,2-GDN | $T_{max}$ (min) 1,2-GDN | Reference |
|---|---|---|---|---|---|
| Dog | 0.3 (1st) | Vaginal | 1.24 | 5 | Present study |
| Dog | 0.3 (2nd) | Vaginal | 1.54 | 10 | Present study |
| Dog | 0.3 (1st) | Vaginal | 0.64 | 20 | Present study |
| Dog | 0.3 (2nd) | Vaginal | 1.73 | 10 | Present study |
| Dog | 0.25 mg/kg | Oral | 85.4 | 28 | Lee[1] |
| Dog | 0.025 mg/kg | Intravenous | 25.5 | 3 | Lee[1] |
| Dog | 0.25 mg/kg | Intravenous | 150 | 4 | Lee[1] |

[1]Lee FW, et al., J Pharmacol Exp Ther, 1990; 255 (3): 1222-1229

TABLE 8

Comparison of 1,3-GDN after two intravaginal doses with other dosing routes

| Species | Dose (mg) Nitroglycerin | Route | $C_{max}$ (ng/mL) 1,3-GDN | $T_{max}$ (min) 1,3-GDN | Reference |
|---|---|---|---|---|---|
| Dog | 0.3 (1st) | Vaginal | 0.30 | 5 | Present study |
| Dog | 0.3 (2nd) | Vaginal | 0.50 | 10 | Present study |
| Dog | 0.3 (1st) | Vaginal | 0.28 | 20 | Present study |
| Dog | 0.3 (2nd) | Vaginal | 0.50 | 10 | Present study |
| Dog | 0.25 mg/kg | Oral | 55.7 | 27 | Lee[1] |
| Dog | 0.025 mg/kg | Intravenous | 2.82 | 3 | Lee[1] |
| Dog | 0.25 mg/kg | Intravenous | 37.8 | 7 | Lee[1] |

[1]Lee FW, et al., J Pharmacol Exp Ther, 1990; 255 (3): 1222-1229

Buprenorphine

Buprenorphine (FIG. 4) was rapidly absorbed in both animals ($T_{max}$ at t=10 and 20 minutes, respectively). The elimination of Buprenorphine was relatively slow (at 120 minutes almost 50% of the $C_{max}$ was still found in plasma). Interestingly, the second administration of Buprenorphine did not result in higher $C_{max}$ values and also the $T_{max}$ was delayed when compared to the first dose. The plasma concentrations of Buprenorphine were more than four times higher for one animal than for the other one.

Peak levels of Buprenorphine (Table 9) given intra-vaginally in the present study are in the same order as those observed following (higher) doses of Buprenorphine via subcutaneous administration (Nunamaker E A, et al., J Am Assoc Lab Anim Sci, 2014; 53(5): 494-501). In comparison with data obtained from studies in humans, the plasma concentrations observed in the present study are reached considerably faster and are considerably higher than those observed after buccal, sublingual or transdermal dosing in man. Only intravenous dosing in man is comparable to intra-vaginal dosing in the dog with respect to $T_{max}$ observed (Kuhlman J J, et al., J.Anal. Toxicol, 1996; 20: 369-378).

TABLE 9

Comparison of Buprenorphine after two intravaginal doses with other dosing routes

| Species | Dose (mg) | Route | $C_{max}$ (ng/mL) | $T_{max}$ (min) | Reference |
|---|---|---|---|---|---|
| Dog | 0.3 (1st) | Vaginal | 6.8 | 10 | Present study |
| Dog | 0.3 (2nd) | Vaginal | 4.8 | 20 | Present study |
| Dog | 0.3 (1st) | Vaginal | 1.4 | 15 | Present study |
| Dog | 0.3 (2nd) | Vaginal | 0.9 | 20 | Present study |
| Dog | 0.2 mg/kg | Subcutaneous | 19.6 | 17 | Nunamaker[1] |
| Human | 0.3 | Buccal | 0.47 | Not reported | RxList.com |
| Human | 0.4 | Sublingual | 0.65 | 90-360 | Bullingham[2] |
| Human | 10.0 | Dermal | 0.2 | Not reported | RxList.com |
| Human | 1.2 | Intravenous | 38.0 | 5 | Kuhlmann[3] |
| Human | 4.0 | Sublingual | 3.3 | 45 | Kuhlmann[3] |
| Human | 4.0 | Buccal | 2.0 | 45 | Kuhlmann[3] |

[1]Nunamaker EA, et al., J Am Assoc Lab Anim Sci, 2014; 53 (5): 494-501
[2]Bullingham RE, et al., Br J Clin Pharmacol, 1982; 13 (5): 665-673
[3]Kuhlman JJ, et al., J.Anal. Toxicol, 1996; 20: 369-378

Nicotine

Nicotine (FIG. 5) showed very fast absorption profiles with $T_{max}$=<5 minutes for both animals, the $C_{max}$ for one of the animals was more than 4-times higher than the $C_{max}$ observed for the other animal, which was also confirmed by differences in clinical signs observed for both animals. After the second dose, absorption was very fast again. Following the second dose the $C_{max}$ values for both animals were similar. The elimination of nicotine was again very fast: the plasma concentrations returned to baseline levels within 120 minutes after the second dose.

Intra-vaginally applied nicotine is absorbed very rapidly ($T_{max}$ at 5 and 10 min, the first sampling points) and efficiently. Peak levels are comparable to those obtained after smoking or gum chewing (see Table 10 for comparison) in humans. Very rapid absorption is a prerequisite for "smoking-like reinforcing properties" of nicotine, thus increasing its efficacy in smoking cessation.

TABLE 10

Comparison of Nicotine after two intravaginal doses with other dosing routes

| Species | Dose (mg) | Route | $C_{max}$ (ng/mL) | $T_{max}$ (min) | Reference |
|---|---|---|---|---|---|
| Dog | 2.5 (1st) | Vaginal | 214 | 5 | Present study |
| Dog | 2.5 (2nd) | Vaginal | 168 | 10 | Present study |
| Dog | 2.5 (1st) | Vaginal | 32 | 5 | Present study |
| Dog | 2.5 (2nd) | Vaginal | 111 | 10 | Present study |
| Dog | 75 | Oral | 14 | 120 | Matsushima[1] |
| Dog | 33 | Oral | 15 | 60 | Matsushima[1] |
| Dog | 31 | Oral | 26 | 60 | Matsushima[1] |
| Dog | 148 | Oral | 36 | 60 | Matsushima[1] |
| Dog | 64 | Oral | 27 | 120 | Matsushima[1] |
| Dog | 57 | Oral | 32 | 30 | Matsushima[1] |
| Human | 2.0 | Intrapulmonary | 49 | 2 | Russell[2] |
| Human | 4.0 | Oral (gum) | 40 | 30 | Russell[2] |

[1] Matsushima D, et al., J Pharm Sci, 1995; 84 (3): 365-369;
[2] Russell MA, et al., Br Med J, 1976; 6017, 1043-1046

Lorazepam

Lorazepam (FIG. 6) administration resulted in similar $C_{max}$ values for both animals after both dose administrations, although the second administration resulted in higher $C_{max}$. The $T_{max}$ values after both administrations were 10 and 20 minutes for both animals. After both administrations, the plasma concentration of Lorazepam returned to baseline within 120 min after administration. Similar Lorazepam concentrations were observed for both animals.

Intra-vaginal administration of lorazepam resulted in rapid peak levels that are only slightly below peak levels in humans after various routes of administration (Table 11). Except for IV, the other dosing routes in humans appear to have considerably higher $T_{max}$ values.

TABLE 11

Comparison of Lorazepam after two intravaginal doses with other dosing routes

| Species | Dose (mg) | Route | $C_{max}$ (ng/mL) | $T_{max}$ (min) | Reference |
|---|---|---|---|---|---|
| Dog | 0.8 (1st) | Vaginal | 4.0 | 5 | Present study |
| Dog | 0.8 (2nd) | Vaginal | 7.0 | 10 | Present study |
| Dog | 0.8 (1st) | Vaginal | 2.8 | 10 | Present study |
| Dog | 0.8 (2nd) | Vaginal | 7.8 | 10 | Present study |
| Human | 2.0 | Oral | 33.4 | 55 | Blin1 |
| Human | 2.0 | Intravenous | 47.6 | 6 | Wermeling2 |
| Human | 2.0 | Intramuscular | 22.6 | 180 | Wermeling2 |
| Human | 2.0 | Nasal | 33.4 | 55 | Wermeling2 |

1Blin O, et al., Clinical Neuropharmacology, 2001; 24, 2: 71-81
2Wermeling DPH, et al., J Clin Pharmacol, 2001; 41: 1225-1231

CONCLUSIONS

In conclusion, absorption after intra-vaginal administration was confirmed for all test compounds, including GnRH, a native peptide with a molecular weight of 1212. For Nitroglycerin, no detectable concentrations of the parent compound could be observed. However, analysis of two well-known metabolites showed rapid and efficient absorption, implying fast Nitroglycerin absorption as well.

Whereas most compounds (Oxybutynin HCl, GnRH, Buprenorphine and Nicotine) showed relatively large differences in observed $C_{max}$ values in the two animal, lorazepam administration showed similar concentration profiles for both animals tested. In general, the $T_{max}$ values varied only slightly between animals within groups, and for most of the test compounds the absorption was very fast, making the vaginal route an interesting alternative for more conventional dosing routes.

All in all, the results of the present study indicate (very) fast absorption for all 6 compounds tested. It should be noted that the Cmax at the time of the first blood sampling of 5 minutes (and subsequent lower concentrations at later samplings) certainly missed the exact Tmax that must have been earlier than at the 5 minute point. Furthermore, the very fast physiological and systemic reaction of the dogs after administration of nitroglycerin, nicotine and buprenorphine gave the earliest clinical indications of fast systemic vaginal absorption of the compounds in the circulatory system.

The invention claimed is:

1. A method of administering a therapeutically active compound for the treatment of a medical condition, the method comprising:
    administering the therapeutically active compound in liquid formulation via the vagina by using an intravaginal ring configured to provide a detectable level in blood or plasma in 1 hour or less; wherein the intravaginal ring comprises a first rigid member having a first and second end, a second rigid member having a third and fourth end, a first flexible member coupled between the first and third ends, and a flexible part coupled between the second and fourth ends;
    wherein at least one of the first flexible member and the flexible part is at least partially elastic, wherein the elasticity of the at least one of the first flexible member and the flexible part is such that:
    the ring can be squeezed to transform a shape of the device from an extended shape to a collapsed shape for allowing the ring to be inserted into a vagina of a user;
    the device is pre-biased to assume the extended shape when little to no external force is being applied thereto, said extended shape corresponding to a substantially oval or annular ring shape;
    the device assumes a shape substantially corresponding to the extended shape when the device is placed and released at or near the fornix posterior vaginae of a user;
    wherein the first rigid member and/or second rigid member comprises a reservoir holding the therapeutically active compound to be delivered, an opening, and a pump for pumping the therapeutically active compound out of said opening; and a diagnostic mechanism for performing an intravaginal diagnosis or measurement therefor.

2. The method as claimed in claim 1, wherein the therapeutically active compound is selected from the group consisting of oxybutynin and other anti-muscarinic compounds, gonadotropin-releasing hormone (GnRH) and derivatives, both agonists and antagonists, nitroglycerin and other directly or indirectly acting cGMP enhancers, buprenorphine and other agonistic, antagonistic or partial (ant)agonistic opioids, nicotine and derivatives, lorazepam and other benzodiazepines, insulin and other blood glucose regulating compounds, FSH and other hormones for ovulation stimulation, pramipexol and other dopamine agonists, oxytocin and other hypothalamic peptides.

3. The method as claimed in claim 1, wherein the compound is GnRH and the medical condition is infertility, and the dosage administered by the intravaginal ring is between 10 µg and 2 mg per 90-120 minutes.

4. The method as claimed in claim 1, wherein the compound is oxybutinin and the medical condition is Overactive Bladder (OAB) and the daily dosage administered by the intravaginal ring is between 0.1 and 30 mg over divided doses.

5. The method as claimed in claim 1, wherein the compound is nitroglycerin and the medical condition is of cardiac or gynecological origin and the dosage administered by the intravaginal ring is between 0.1 and 10 mg per dose, depending on symptoms.

6. The method as claimed in claim 1, wherein the compound is buprenorphine and the medical condition is moderate to severe pain or opioid dependence and the dosage administered by the intravaginal ring is between 50 µg and 2 mg per day over divided doses.

7. The method as claimed in claim 1, wherein the compound is nicotine and the medical condition is smoking cessation or mild cognitive impairment and the daily dosage administered by the intravaginal ring is between 1 and 30 mg over divided doses.

8. The method as claimed in claim 1, wherein the compound is lorazepam and the medical condition is insomnia and the dosage administered by the intravaginal ring is between 0.1 and 10 mg, one before bedtime and one during sleep.

9. The method as claimed in claim 1, wherein the compound is insulin and the medical condition is diabetes and the dosage administered by the intravaginal ring is based upon individual patient sensitivity.

10. The method as claimed in claim 1, wherein the compound is FSH and/or an GnRH antagonist and/or LH and/or HMG and the medical condition is infertility and the dosage administered by the intravaginal ring is based upon individual patient sensitivity.

11. The method as claimed in claim 1, wherein the compound is pramipexole, for the medical indication Parkinson's disease and restless legs, or hyperprolactinemie and the dosage administered by the intravaginal ring is based upon individual patient sensitivity and varies between 0,3 and 10 mg/day.

12. The method as claimed in claim 1, wherein the compound is administered in a pulsatile manner or on-demand.

13. The method as claimed in claim 1, wherein the compound is a glucocorticoid for circadian administration in case of oncology.

14. The method as claimed in claim 1, wherein the compound is an immunotherapeutic compound for treatment of an oncological condition.

15. The method as claimed in claim 1, wherein the intravaginal ring further comprises one or more sensors for measuring parameters that can be used in the diagnosis of a medical condition.

16. The method as claimed in claim 15, wherein the sensor is selected from biochemical sensor, temperature sensor, glucose sensor, electromyogram (EMG) or pressure contraction sensor, cardiovascular sensor.

17. The method as claimed in claim 1, wherein the intravaginal ring comprises one or more of the following features: a battery, a transmitter configured for wireless transmission of measurement data corresponding to measurements performed by the sensor and/or measurement data or diagnosis information outputted by the diagnostic sensor, a receiver for wirelessly receiving control commands for remote control of at least one of the pump, the sensor, and the diagnostic device, a transceiver unit combining the receiver and transmitter.

18. The method as claimed in claim 1, wherein the intravaginal ring is configured to administer the therapeutically active compound in dosages of 50 µl.

19. The method as claimed in claim 1, wherein the intravaginal ring comprises a reservoir sized to contain a restricted amount of the therapeutically active compound in liquid formulation that ranges 1 ml to 3 ml.

* * * * *